United States Patent [19]

Vollhardt et al.

[11] 4,328,343
[45] May 4, 1982

[54] COBALT-CATALYZED ONE-STEP SYNTHESIS OF ANNULATED PYRIDINES

[75] Inventors: K. Peter C. Vollhardt; Alaric Naiman, both of Berkeley, Calif.

[73] Assignee: The United States of America as represented by the Department of Health and Human Services, Washington, D.C.

[21] Appl. No.: 54,926

[22] Filed: Jul. 5, 1979

Related U.S. Application Data

[63] Continuation of Ser. No. 886,119, Mar. 13, 1978, abandoned.

[51] Int. Cl.³ ............... C07D 217/14; C07D 221/04; C07D 455/04
[52] U.S. Cl. .................................. 546/145; 546/94; 546/139; 546/144; 546/147
[58] Field of Search ............... 546/94, 112, 139, 144, 546/145, 147

[56] References Cited

FOREIGN PATENT DOCUMENTS 49-66684  6/1974  Japan ................................. 546/139

OTHER PUBLICATIONS

Hackh's Chem. Dictionary, p. 62, (1972), McGraw-Hill Co., N.Y.
S. Archer, J. Org. Chem. 16, 430-1, (1951).

R. Hilliard et al., Chem. Abstracts 84:30726t, (1976), Transition Metal Catalyzed Acetylene Cyclizations.
T. Cairns et al., J. Amer. Chem. Soc., 74:3989-3992, (1952), Synthesis of Pyrimidines and Pyridines from Acetylene and Nitriles.

Primary Examiner—Donald G. Daus
Assistant Examiner—Diana G. Rivers
Attorney, Agent, or Firm—John S. Roberts, Jr.

[57] ABSTRACT

A method of synthesizing fused ring pyridines (annulated) by co-oligomerization of $\alpha,\omega$-diynes with about molar equivalents of nitriles using a $Co^{+1}$ catalyst preferably cyclopentadienyl cobalt dicarbonyl. Additionally, new compounds of tricyclic quinolizine-4-ones were produced where excess cyanoacetic ester starting materials were utilized (about 2:1 equivalent nitriles:-diyne). The results with the catalyst employed indicated a stepwise mechanism in which cobalt(I) catalyst first forms a metallocycle intermediate derived from the bisacetylene. This cobalt(III) intermediate reacts preferentially with nitriles to give the product annulated pyridines in good yield. Generally, preferred conditions indicated roughly molar equivalents of reactants with no substantial excess of either reactant for the bicyclic compounds. Preferred conditions include a moderate temperature (solvent reflux temperature) and a preferred solvent such as BTX-type solvent (xylene) or an alkane (N-octane) under an inert blanket (nitrogen) for a multi-day period.

3 Claims, No Drawings

COBALT-CATALYZED ONE-STEP SYNTHESIS OF ANNULATED PYRIDINES

This is a continuation of application Ser. No. 886,119, filed Mar. 13, 1978 now abandoned.

The present invention relates to new methods and products wherein the pyridine nucleus is incorporated into a more complex structure and these compounds are known as annulated pyridines. The synthesis of annulated pyridines in the past has relief on condensations, cyclo additions and special methods. Fusion of rings in this heterocycle has generally been achieved by the use of intramolecular Friedel-Crafts cyclizations.

This invention relates to a novel approach based upon cobalt-catalyzed co-oligomerization of δ, ω-diynes with nitriles. The cobalt catalyst of choice is cyclopentadienyl cobalt dicarbonyl.

PRIOR ART STATEMENT

The prior art relative to the present invention shows utilization of monoacetylenes but not utilizing the present diacetylenes.

Cairns et al, *Journal of American Chemical Society*, 74:3989–3992 (1952).

Wakatsuki, *Synthesis*, January 1976, pages 26–28.

Wakatsuki et al, *Tetrahedron Letters*, 36:3383–84 (1973).

Naiman and Vollhardt, *Angewante Chemie* (Int. Ed. (Engl) 16:708–709, No. 10 (1977).

The preparation of substituted pyridines from monoacetylenes and nitriles using cobalt catalysts or reagents is old. However, yields were unimpressive and the product and selectivity was low and the product mixtures were synthetically useless. In the present approach based on the synthesis of 2-substituted annulated pyridines by a cobalt-catalyzed co-oligomerization of diacetylenes with nitriles allows in one step the formation of oligoheterocyclic systems with pronounced chemo- and regio-selectivity which is quite tolerant of functional groups on the nitrile and permits the reaction to form medium-sized (seven membered) rings. A preferred catalyst is cyclopentadienyl cobalt dicarbonyl, a group VIII carbonyl catalyst.

In the following experiments the reaction of diyne with about an equal equivalent of nitrile was observed to produce an annulated substituted pyridine structure (cf. Table 1, post).

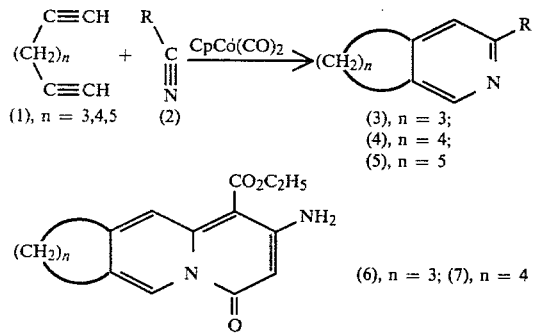

Cyclization of (1) where n=3 or 4, utilizing excess cyanoacetic ester, results in a novel 7,8-annulated 2-amino-4-oxo-4H-quinolizine-1-carboxylate. In this case the extra measure of cyanoacetic ethyl ester converts the intermediate 3-(tetrahydroisoquinoline)acetate by condensation with a second equivalent of nitrile to form a 3-ring heterocycle. New compounds are produced by this method which are 7,8-annulated 2-amino-4-oxo-4H-quinolizine-1-carboxylates (6,7 above).

Additional compounds synthesized by the process of this invention are expressed by the following equation:

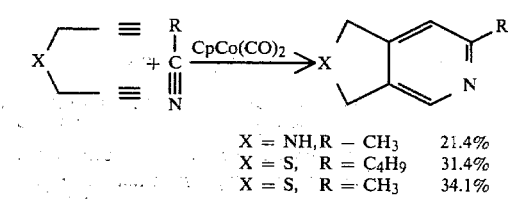

X = NH, R — CH₃   21.4%
X = S,  R = C₄H₉  31.4%
X = S,  R = CH₃   34.1%

In this specification and claims, the term "lower alkyl" is defined as $C_1$–$C_6$ and may be either straight or branched chain.

TABLE 1

| (2) | R | (3)–(7) | n | Yield [%] |
|---|---|---|---|---|
| (2a) | n-C₄H₉ | (3a) | 3 | 67 |
| (2b) | C₆H₅ | (3b) | 3 | 56 |
| (2a) | n-C₄H₉ | (4a) | 4 | 77 |
| (2b) | C₆H₅ | (4b) | 4 | 70 [5] |
| (2c) | CH₃ | (4c) | 4 | 81 [6] |
| (2d) | CH₂OCH₃ | (4d) | 4 | 62 |
| (2e) | CO₂C₂H₅ | (4c) | 4 | 5.9 [7] |
| (2f) | CH₂CO₂C₂H₅ | (4f) | 4 | 47 |
| (2g) | CH₂CH₂CN | (4g), (4h) | 4 | [a] |
| (2h) | C₆F₅ | (4i), (4j), (4k) | 4 | 2.7 [b,c] [8] |
| (2i) | C(CH₃)₃ | (4l) | 4 | 47 |
| (2j) | CH₂C₆H₅ | (4m) | 4 | 61 |
| (2k) | NH₂ | (4n) | 4 | 3 |
| (2a) | n-C₄H₉ | (5a) | 5 | 43 |
| (2b) | C₆H₅ | (5b) | 5 | 54 |
| (2f) | CH₂CO₂C₂H₅ | (6) | 3 | 37 [d] |
| (2f) | CH₂CO₂C₂H₅ | (7) | 4 | 22 [d] |

[a] Products (4g) and (4h) with R = CH₂CH₂CN (yield 30%) and CH₂CH₂—3-(5,6,7,8-tetrahydro)isoquinolyl (yield 19%)

[b] Mixture of the products (4i), (4j), and (4k) with R = C₆F₅, C₆F₄H and C₆F₃H₂ (3.5:5.5:1)

[c] Analyzed by GC/mass spectroscopy on a DuPont 492-1 instrument interfaced with a Varian Aerograph Model No. 204 (linear temperature programmer) equipped with a 20' + 0.03" glass capillary column (ca. 600 cm × 0.1 cm) packed with 3% Dexsil 300 on 80/100 gas chrom Q.

[d] With excess (2f).

The results in Table 1 above illustrate that strongly electron-withdrawing groups bound directly to the cyano carbon appear to be disadvantageous and also that large excess of any one reactant (in particular nitrile) is unnecessary and does not lead to improved yields.

The R group at the 2 position of the annulated pyridine produced thus may be -lower alkyl, -substituted lower alkyl, -lower alkyl ethers, -carboxy alkyl, -lower alkyl ester, -lower alkyl nitrile, -pentafluoromonoaryl, or -monoaryl.

Pronounced regioselectivity is observed in the reaction of 1,7-decadiyne (8, below) with valeronitrile (2a) resulting in the preferred formation of product (4m), at the expense of (4n) (17:1 ratio).

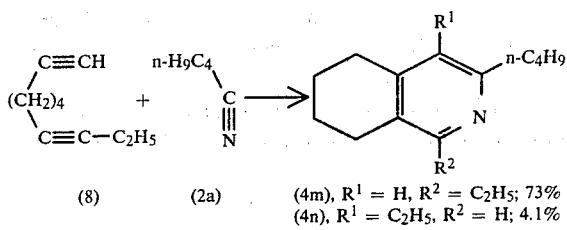

(8)   (2a)   (4m), $R^1$ = H, $R^2$ = $C_2H_5$; 73%
              (4n), $R^1$ = $C_2H_5$, $R^2$ = H; 4.1%

PROCESS TECHNIQUES

In the laboratory procedures, syringe pump techniques were utilized. Furthermore, work up of the reaction mixture involved extraction with diluent acid and simple column chromatography on silica or alumina. Side products consisted of oligomers derived from the starting diyne. Analytically pure samples were obtained by distillation, sublimation, recrystallization, or preparative gas chromatography (10′ × 3/8″ glass, 20% SE 30 on 60/80 Chrom W-AW, 240° C.). The structures of products 2–7 were in accord with spectral data (m/e, NMR, IR). Yields are subject to some variation in yield with solvent, temperature (for example the yield of 2c formed at 80° is 30%), reaction time, and mode of addition (e.g., variations in concentrations of the various reactants in syringe and flask). A set of preferred reaction conditions consists of a solution of diyne in n-octane being added to a refluxing solution of nitrile in n-octane under $N_2$ over a multi-day period. Monosubstituted diyne 1a was obtained from the disodium salt of 1,7-octadiyne and one equivalent ethyl iodide in liquid $NH_3$ followed by p.g.l.c. (column temperature 170° C.) in ca. 50% yield.

EXAMPLE

Ethyl 3-(5,6,7,8-tetrahydroisoquinoline)acetate (4f).

A solution of 1,7-octadiyne (1), n=4, (650 μl, 5.00 mmol), cyanoacetic ester (2f) (531 μl, 5.00 mmol) and $(C_5H_5)Co(CO)_2$ (63 μl, 0.50 mmol) in xylene (15 ml) was added over 117 h (by syringe pump) to o-xylene (15 ml) warmed to reflux under $N_2$ (all reagents deoxygenated).

After removal of solvent under reduced pressure, the reaction mixture was chromatographed on silica gel (60 g; ether elution). The crude product was microdistilled (85°–105° C./0.02 torr) to give a clear oil, analytically pure (510 mg = 47.1%).

We claim:

1. A method of synthesizing annulated pyridines which comprises the step of reacting about equal equivalent quantities of the following reactants in the presence of cyclopentadienyl cobalt dicarbonyl, CpC(CO)$_2$, to form annulated pyridines

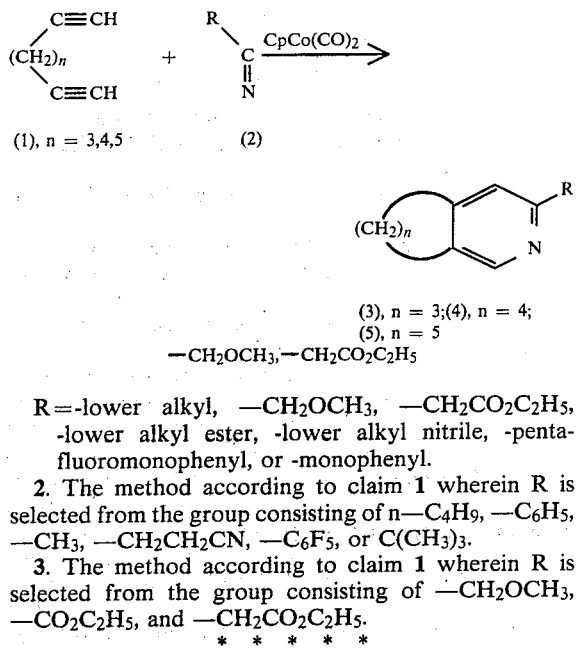

(1), n = 3,4,5   (2)

(3), n = 3; (4), n = 4; (5), n = 5
—CH$_2$OCH$_3$, —CH$_2$CO$_2$C$_2$H$_5$

R = -lower alkyl, —CH$_2$OCH$_3$, —CH$_2$CO$_2$C$_2$H$_5$, -lower alkyl ester, -lower alkyl nitrile, -pentafluoromonophenyl, or -monophenyl.

2. The method according to claim 1 wherein R is selected from the group consisting of n—C$_4$H$_9$, —C$_6$H$_5$, —CH$_3$, —CH$_2$CH$_2$CN, —C$_6$F$_5$, or C(CH$_3$)$_3$.

3. The method according to claim 1 wherein R is selected from the group consisting of —CH$_2$OCH$_3$, —CO$_2$C$_2$H$_5$, and —CH$_2$CO$_2$C$_2$H$_5$.

* * * * *

UNITED STATES PATENT OFFICE
CERTIFICATE OF CORRECTION

Patent No. 4,328,343                    Dated May 4, 1982

Inventor(s)  K. Peter C. Vollhardt and Alaric Naiman

It is certified that error appears in the above-identified patent and that said Letters Patent are hereby corrected as shown below:

Claim 1 just beneath the formula structures and before the definitions of R, delete the line:

$-CH_2OCH_3$, $-CH_2CO_2C_2H_5$

Signed and Sealed this

Tenth Day of August 1982

[SEAL]

Attest:

GERALD J. MOSSINGHOFF

*Attesting Officer*      *Commissioner of Patents and Trademarks*